United States Patent
Aggarwal

(10) Patent No.: US 6,605,278 B1
(45) Date of Patent: Aug. 12, 2003

(54) USES OF TRANK, A NOVEL SECRETORY CYTOKINE

(75) Inventor: Bharat B. Aggarwal, Houston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/375,907

(22) Filed: Aug. 17, 1999

Related U.S. Application Data

(60) Provisional application No. 60/097,006, filed on Aug. 18, 1998, now abandoned.

(51) Int. Cl.⁷ ............................................. A61K 39/395
(52) U.S. Cl. ................................ 424/145.1; 530/389.2; 530/387.9; 514/2
(58) Field of Search .................... 424/145.1; 530/389.2, 530/387.9; 514/2

(56) References Cited

FOREIGN PATENT DOCUMENTS

WO    WO 96/39424    * 12/1996

* cited by examiner

*Primary Examiner*—Yvonne Eyler
*Assistant Examiner*—Eileen B. O'Hara
(74) *Attorney, Agent, or Firm*—Benjamin Aaron Adler

(57) ABSTRACT

The present invention provides methods for the therapeutic application of TRANK, a novel cytokine. TRANK is secreted by cells and activates NF-κB, c-Jun N-terminal kinase (JNK) and downstream gene products. Provided is a method of inhibiting NF-κB activation in an individual in need of such treatment, comprising the step of administering an effective dose of an anti-TRANK antibody to said individual.

3 Claims, 9 Drawing Sheets

```
  1  MEALP---LLAATTPDHGRHRSCFCLPLLLPLLPAGAVQGWETEERPRTREEECHPYAGGQVYPGBASPV  TRANK
  1  MSS-----------------------------------------------------------------  NKEF A
  1  MSS-----------------------------------------------------------------  NKEF B
  1  MSS-----------------------------------------------------------------  PAG
  1  MAAAGRLLWSSVA---RHASAISRSI-----SASTVL------RPVASRRTCL---TDILWSASAQGK  MER5

68  SVADHSLHLSEAKISKPAEYWEGTAVI-DGKPKELKLTDYRGKYLVLFFYPLDFTFVCPTEIIAFGDRL  TRANK
  4  ---------GNAKIGHPAPNFKATAVMPGGQFKDISLSDYKGKYVVFFFYPLDFTFVCPTEIIAFSDRA  NKEF A
  4  ---------GNARIGKPAPDFKATAVV-DGAFKEVKLSDYKGKYVVLFFYPLDFTFVCPTEIVAFSDKA  NKEF B
  4  ---------GNAKIGHPAPDFKATAVMPGGQFKDISLSDYKGKYVVFFFYPLDFTFVCPTEIIAFSDKA  PAG
 53  SAFSTSSSFHTPAVTQHAPYKEGTAVN-NGEFKELSLDDFKGKYLVLFFYPLDFTFVCPTEIVAFSDKA  MER5

136  KEFRSINTEVVACSVDSQFTHLAWINTPRKQGGLGPMNIPLLSDLTHQISKDYGVYLEDSGHTLRGLFI  TRANK
 64  EEFRKINCQVIGASVDSHFCHLAWVNTPKKQGGLGPMNIPLVSDPKRTIAQDYGVLKADEGISFRGLFI  NKEF A
 63  EDFRKLGCEVLGVSVDSQFTHLAWINTPRKEGGLGPLNIPLLSDPKRTIAQDYGVLKTDEGIAYRGLFI  NKEF B
 64  EEFRKLNCQVIGASVDSHFCHLAWVNTPKKQGGLGPMNIPLVSDPKRTIAQDYGVLKADEGISFRGLFI  PAG
121  NTFHDVNCEVVAVSVDSHFSHLAWINTPRKNGGLGHMNITLVSDIKQSSRDYGVLLESAGIALRGLFI  MER5

205  IDDKGILRQITLNDLPVGRSVDETLRLVQAFQVTDKHGEVCPAGWKPGSETIIPDPAGKLKYFDKLN   TRANK  (SEQ ID NO: 1)
133  IDDKGILRQITLNDLPVCPKGVDEALRLVQAFQYTDKHGEVCPAGWKPGSDTIKPNVDDSKEYFSK-QK NKEF A  (SEQ ID NO: 2)
132  IDGKGVILRQITLNDLPVGRSVDEALRLVQAFQYTEERKGEVCPAGWKPGSDTIKPNVDDSKEYFSK-HN NKEF B  (SEQ ID NO: 3)
133  IDDKGILRQITLNDLPVGRSVDEALRLVQAFQYLKQGEVCPAGWKPGSDTIKPNQRSKEYFSK-QK   PAG    (SEQ ID NO: 4)
190  IDPNGVVKHLSVNDLPVGRSVEETLRLVKAFQFVETHGEVCPANWTPESPTIKPSPTASKEYFEKVHQ MER5   (SEQ ID NO: 5)
```

Fig. 1A

USES OF TRANK, A NOVEL SECRETORY CYTOKINE

CROSS-REFERENCE TO RELATED APPLICATIONS

This application claims benefit of priority of U.S. provisional application Serial No. 60/097,006, filed Aug. 18, 1998, now abandoned.

BACKGROUND OF THE INVENTION

1. Field of the Invention

The present invention relates generally to the fields of cytokine biology and therapeutic applications of cytokines. More specifically, the present invention relates to uses of the novel cytokine TRANK.

2. Description of the Related Art

Most living organisms have evolved several antioxidant proteins and peptides to counteract the damaging effects of reactive oxygen species. These include superoxide dismutase, glutathione, glutaredoxin, thioredoxin, thioredoxin reductase and thioredoxin peroxidase. Most of these proteins have been well conserved during evolution (1, 2). Almost all antioxidant proteins are cytoplasmic proteins, and can thus only protect those cells producing them.

Natural killer cell-enhancing factor (NKEF) is a protein that was discovered recently and has been found to possess antioxidant properties that protect proteins and DNA from oxidative damage (3). NKEF is a 24-kDa protein that was initially found to be abundant in red blood cells and to augment natural killer (NK) cell-mediated cytotoxicity (4). This protein is encoded by two distinct genes, nkef-A and nkef-B, which are 71% identical in their nucleotide sequence and 88% identical in their deduced amino acid sequence (5).

nkef-B is a gene for thioredoxin peroxidase, and transfection of cells with this gene can block apoptosis (19). Similarly, overexpression of another thioredoxin peroxidase gene, AOE372, blocked the activation of the nuclear transcription factor kappa B (NF-κB) and degradation of the inhibitory subunit of NF-κB, IκBα, induced by tumor necrosis factor (TNF) and phorbol ester (2). This is consistent with the antioxidant properties of the protein product of this gene (1).

Activation of NF-κB is induced by many agents, such as inflammatory cytokines (e.g., tumor necrosis factor (TNF), lymphotoxin (LT), and interleukin (IL)-1), mitogens, bacterial products, protein synthesis inhibitors, $H_2O_2$-induced oxidative stress, ultraviolet light, and phorbol esters. The inhibition of NF-κB is an important step in the treatment of various pathological conditions which result from the activation of NF-κB by these agents. Substances which can inhibit the activation of NF-κB may be used for therapeutic treatment for pathological conditions including toxic/septic shock, graft vs. host reaction, acute inflammatory conditions, acute phase response, viral infection, radiation damage susceptibility, atherosclerosis, and cancer.

Also important in the consideration of the effects of activation of NF-κB are downstream gene products, most prominently inducible nitric oxide synthase (iNOS) and intracellular adhesion molecule-1 (ICAM-1). iNOS is one of the major enzymes involved in the synthesis of nitric oxide (NO), a highly reactive free radical. It has emerged as an important mediator of inflammatory responses. For example, tumor necrosis factor (TNF), in combination with nitric oxide and/or other cytokines (such as interleukin-1 and interleukin-6), may bring about the tissue destruction observed in certain autoimmune diseases such as psoriasis, rheumatoid arthritis, osteoarthritis and other joint diseases.

On a physiological level, nitric oxide is the most potent vasodilator known and is required for a variety of cellular functions. For example, the cytotoxic activity of macrophages is dependent on nitric oxide. The production of nitric oxide in the vascular endothelium regulates blood pressure, and it is a neurotransmitter. Clearly, nitric oxide has beneficial biological functions that serve a variety of physiological processes, however, it also has less salutary effects. nitric oxide is unstable and it inhibits enzymes; intracellular nitric oxide is highly reactive and reacts with other free radicals, molecular oxygen and heavy metals. Persistent high concentrations of nitric oxide can cause DNA damage.

The role of nitric oxide in pathophysiology is thus suggested, but its precise dimensions are not clear. Although nitric oxide might in some way modulate tumor development, it has been unclear whether it inhibits or stimulates tumor growth, angiogenesis or metastasis. With respect to the role of nitric oxide in cancer, it has been observed that breast cancer cell lines, human breast cancer cells and mouse mammary tumor cell lines produce nitric oxide in amounts that correlate with tumor grade. Breast cancer tissue samples have been shown to express iNOS in the infiltrating macrophages of the tumor. Further, p53 expression down-regulates iNOS expression. Additionally, nitric oxide itself directly affects the regulation of p53 gene expression as well as the conformation and activity of the p53 protein. It is possible that nitric oxide induces mutations in p53 that abrogate iNOS regulation, and these could contribute to cell transformation. Excessive nitric oxide production in inflamed tissues might play a role in carcinogenesis by impairing the tumor suppressor function of p53. Further, there have been conflicting reports indicating that nitric oxide can stimulate or inhibit angiogenesis.

Hence, modulation of nitric oxide levels via control of iNOS expression as regulated by NF-κB activation could have far-reaching physiological implications. The prior art is deficient in the description of the uses of secretory cytokines to manipulate NF-κB activation, which may play an important role in inflammatory processes and cellular pathophysiology. The present invention, methods for the control of NF-κB functions by use of a novel secretory cytokine, TRANK, fulfills this long-standing need and desire in the art.

SUMMARY OF THE INVENTION

A novel cytokine polypeptide, termed TRANK, has been previously described (22). This protein is secreted by cells, has a molecular weight of approximately 30 kDa on SDS-PAGE and is further characterized by activation of the nuclear transcription factor NF-κB and downstream gene products (e.g. iNOS or ICAM-1), as well as the activation of c-Jun N-terminal kinase (JNK). Additionally, TRANK has proliferative effects on normal human foreskin fibroblasts.

In one embodiment of the present invention, there is provided a process for utilizing the novel TRANK polypeptide for therapeutic purposes. Examples of such purposes include the stimulation of production of iNOS or ICAM-1 or inhibition of NF-κB or JNK via antibody technology.

In other embodiments of the present invention, there are provided pharmaceutical compositions of TRANK and methods of treating conditions in which insufficient levels of such NF-κB-dependent gene products as iNOS or ICAM-1 are present, comprising the administration of an effective dose of TRANK.

In yet another embodiment of the present invention, there is provided a method for the inhibition of nuclear transcription factor NF-κB for use in the treatment of pathological conditions including toxic/septic shock, graft vs. host reaction, acute inflammatory conditions, acute phase response, viral infection, radiation damage susceptibility, atherosclerosis, and cancer, comprising the step of administering an anti-TRANK antibody to an individual in need of such treatment.

In another embodiment of the present invention, there is provided a method for the inhibition of the synthesis of nitric oxide by inhibiting NF-κB and a downstream gene products, iNOS.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A depicts the deduced amino acid sequence of TRANK (SEQ ID 1) and its homology with NKEF-A (natural killer cell-enhancing factor-A; (SEQ ID 2)), NKEF-B (thioredoxin peroxidase; (SEQ ID 3)), PAG (proliferation associated gene product; (SEQ ID 4)), and MER5 (murine erythroleukemia related; (SEQ ID 5)).

DETAILED DESCRIPTION OF THE INVENTION

Figure 1B:
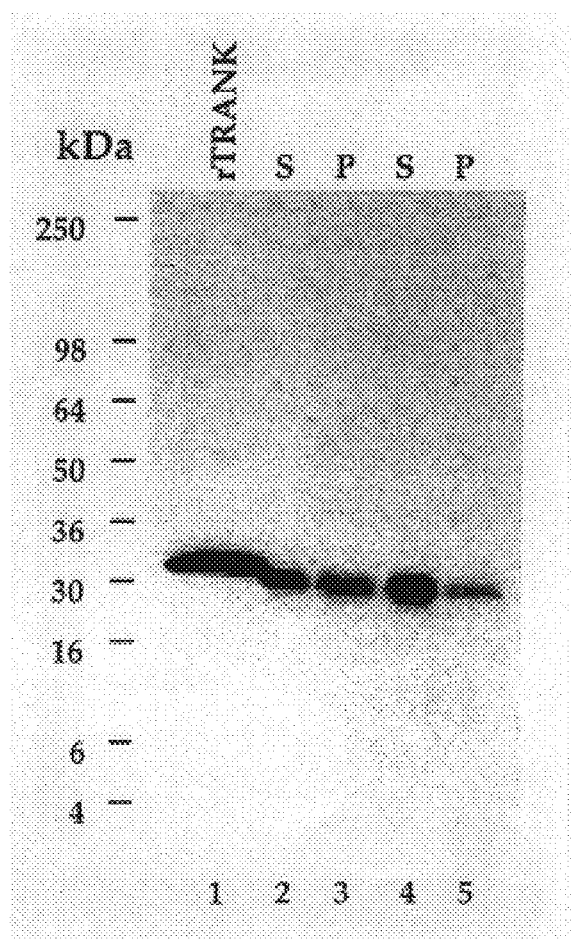
FIG. 1B illustrates results of SDS-PAGE showing purified TRANK (lane 1) and its secretion by Jurkat cells (lanes 2 and 3) and HL-60 cells (lanes 4 and 5). S and P are conditioned media and cell extracts, respectively.

The present invention describes how TRANK, a novel human cytokine, can be used to increase downstream gene products of the transcription factors NF-κB and JNK, most particularly iNOS and ICAM-1 by activation of these transcription factors.

As used herein, the term "nuclear factor NF-κB" or "NF-κB" shall refer to the protein specific to B cells that binds to a specific DNA sequence within the immunoglobulin light chain κ locus enhancer region, and in mammals is a heterodimer consisting of p50 and p65 (Rel-A) proteins. NF-κB plays a central role in various responses, leading to host defense through rapid induction of gene expression, and controls the expression of various inflammatory cytokines, the major histocompatibility complex genes, and adhesion molecules involved in tumor metastasis.

The present invention is directed to a pharmaceutical composition comprised of the human cytokine TRANK and a pharmaceutically acceptable carrier. The present invention is further directed to a method for treating a pathological condition characterized by insufficient levels of iNOS or ICAM-1 comprising the administration of a therapeutically effective amount of TRANK to an individual in need of such treatment.

The dosage of TRANK administered in the methods of the present invention is dependent upon the age, weight, kind of concurrent treatment, if any, and nature of the pathophysiological state. The effective composition useful in the methods of the present invention may be employed in such forms as liposomes or various viral vectors. Generally, the therapeutically effective amount of TRANK is in the dosage range of 0.01–100 mg/kg.

Conversely, the present invention is also directed to a method of inhibition of NF-κB activation, comprising the step of administering an effective dose of an anti-TRANK antibody. The present invention is additionally directed to a method for treating a pathophysiological state in a human wherein said state is characterized by an undesirable level of NF-κB activation, comprising the step of administering to said human an effective dose of an anti-TRANK antibody. Generally, the dose of the anti-TRANK antibody useful in the methods of the present invention is any that inhibits NF-κB activation. A person having ordinary skill in the art of antibody therapy would readily be able to determine an appropriate dose of the anti-TRANK antibody. Representative pathophysiological states characterized by undesirable levels of NF-κB activation include: toxic shock, septic shock, acute phase response, viral infection, radiation susceptibility, atherosclerosis, cancer, acute inflammatory conditions or graft vs. host reaction.

Inhibition of NF-κB activation in turn blocks production of downstream gene products, including iNOS, which is involved in the synthesis of nitric oxide. Thus, the present invention is also directed to a method of inhibiting production of nitric oxide in a human comprising the step of administering an effective dose of an anti-TRANK antibody. As overactivation of nitric oxide can lead to disease states characterized by an undesirable level of nitric oxide production, the present invention is further directed to a method for treating a pathophysiological state in a human wherein said state is characterized by production of an undesirable level of nitric oxide, comprising the step of administering to said human an effective dose of an anti-TRANK antibody. Representative pathophysiological states include: sepsis, cachexia, neoplastic diseases such as Kaposi's sarcoma, cerebral malaria, capillary leak syndrome and autoimmune diseases. Representative autoimmune diseases include systemic lupus erythematosus, rheumatoid arthritis and multiple sclerosis. Representative neoplastic diseases include breast and lung cancer.

Generally, the dose of the antibody useful in the methods of the present invention is any that inhibits the production of nitric oxide in the animal. A person having ordinary skill in the art of antibody therapy would readily be able to determine an appropriate dose of the antibody of the instant invention.

The following examples are given for the purpose of illustrating various embodiments of the invention and are not meant to limit the present invention in any fashion:

EXAMPLE 1
Identification, Cloning, Expression and Purification of Recombinant TRANK TRANK was identified by a systematic comparison of the signal peptide and NKEF sequence homology against the EST database (Human Genome Sciences Inc., Rockville, Md.) and by functional screening assays (6, 7, 8). The sequence encoding the putative natural TRANK protein (aa 32 to 271) was amplified employing standard PCR techniques. The amplified fragment was then purified, digested with NcoI and HindIII, and cloned in a pQE60 *Escherichia coli* expression vector. The cloning, expression, and confirmation of the cloned sequence were performed using standard procedures. The chromosomal localization of TRANK gene was done by the method as described (9).

The protein was purified using $(NH_4)_2SO_4$ and polyethylene glycol precipitation followed by an anion exchange chromatography performed on an HQ50 column (Poros CM20; from PerSeptive Biosystems, Hertfordshire, UK). The purified protein migrated as a single band by SDS-PAGE, and N-terminal amino acid sequence demonstrated that >95% of the purified TRANK contained the expected N-terminal sequence. Endotoxin levels assayed by the Amebocyte Lysate Test (Bio Whittaker, Walkersville, Md.) proved to be less than 16.5 EU/mg protein.

TRANK was shown to exhibit sequence homology to several antioxidant proteins, including NKEF-A, NKEF-B (thioredoxin peroxidase), PAG (Proliferation associated gene product) and MER5 (murine erythroleukemia related) (2, 5) (FIG. 1A). Specifically, the nucleotide sequence of TRANK cDNA was 58% and 56% identical to that of NKEF-A and NKEF-B, respectively. The deduced amino acid sequence showed 66% and 68% homology to that of NKEF-A and NKEF-B, respectively (see FIG. 1A). Unlike NKEF-A and NKEF-B, however, TRANK had a putative N-terminal secretory-signal sequence. Results of western blot analysis of the conditioned media suggested that TRANK is indeed secreted from Jurkat and HL-60 cells (FIG. 1B).

The gene encoding the putative TRANK protein (aa 32 to 271) (FIG. 1A) was amplified using standard PCR techniques and then cloned and expressed in *E. coli* after which the recombinant protein was purified. SDS-PAGE analysis of TRANK showed a single band at around 30 kDa (see FIG. 1B). The size of the recombinant TRANK appeared slightly higher than the natural protein.

EXAMPLE 2
Northern Blot Analysis

Two filters containing approximately 2 mg of poly (A+) RNA per lane from various human tissues (Clontech Labs Inc., Palo Alto, Calif.) were probed with a $^{32}$P-labeled TRANK cDNA. The RNA from a selected panel of human cell lines was also probed using a similar method.

Figure 2A:
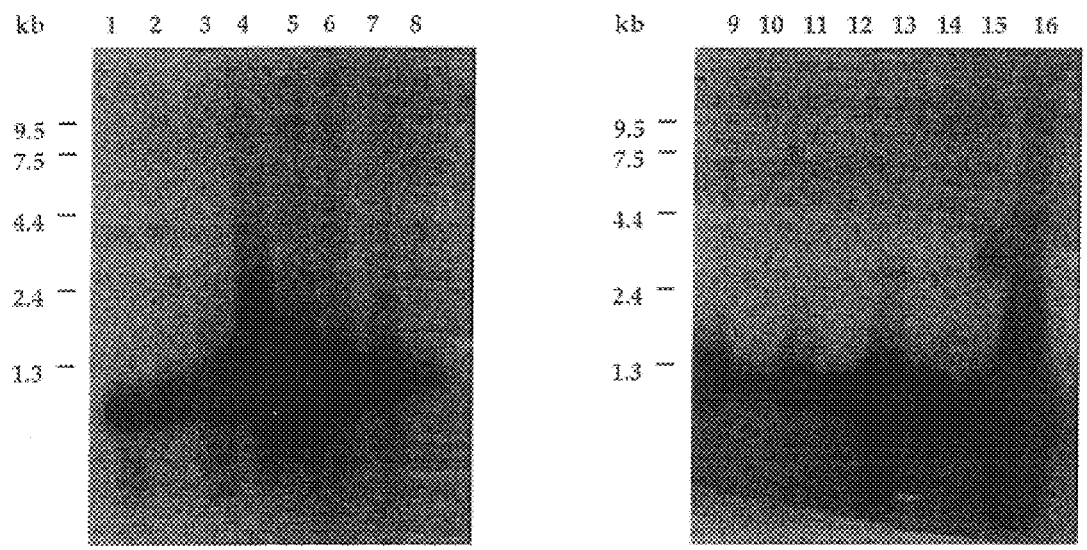
FIG. 2A shows tissue distribution of TRANK mRNA as shown by northern blot analysis. lane 1, spleen; lane 2, thymus; lane 3, prostate; lane 4, testis; lane 5, ovary; lane 6, small intestine; lane 7, colon; lane 8, peripheral blood leukocytes; lane 9, heart; lane 10, brain; lane 11, placenta; lane 12, lung; lane 13, liver; lane 14, skeletal muscle; lane 15, kidney; lane 16, pancreas.
Figure 2B:
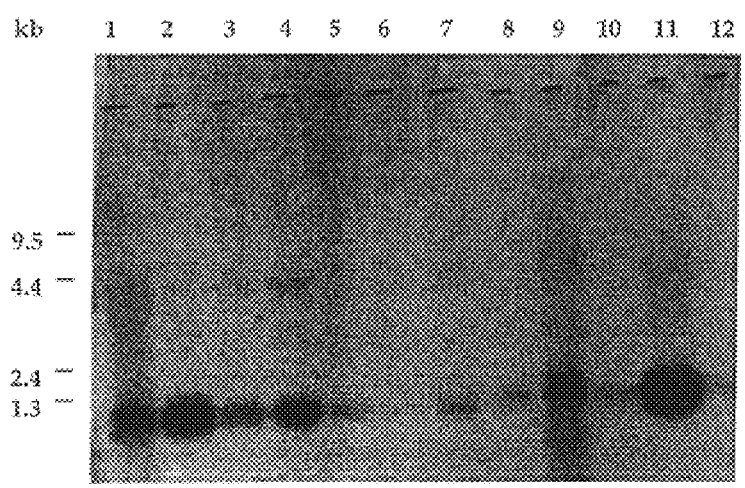
FIG. 2B illustrates expression of TRANK mRNA in various cell lines. Lane 1, Jurkat (T-cell leukemia); lane 2, A293 (embryonic kidney); lane 3, HL60 (promyelocytic leukemia); lane 4, VE 11 (venous endothelium); lane 5, A431 (epidermoid carcinoma); lane 6, VE 9 (venous endothelium); lane 7, Raji (Burkitt lymphoma); lane 8, AE (arterial endothelium); lane 9, THP-1 (monocytic leukemia); lane 10, BUD 8 (skin fibroblast); lane 11, Chang liver (liver); lane 12, CCD-29 (lung fibroblast).

The gene that encodes for human TRANK was mapped to human chromosome Xp21-22.1. Northern blot analysis showed that TRANK was highly expressed in testis, ovary, heart, liver, skeletal muscle and pancreas. Moderate expression was seen in spleen, thymus, prostrate, small intestine, colon, placenta, and lung, and low expression in peripheral blood leukocyte and brain (FIG. 2A). Almost all types of cells among human tumor cell lines transcribed TRANK mRNA. However, T cells (Jurkat), kidney (A-293), endothelial cells (VE 11), and Chang liver cells showed relatively high expression (FIG. 2B).

EXAMPLE 3
Immunoprecipitation and Western Blot Analysis of TRANK

HL-60 and Jurkat cells ($2 \times 10^7$) were grown in culture for 24 h, then conditioned media (10 ml) and cell lysate (2.25 ml) were immunoprecipitated and analyzed by western blot using anti-TRANK polyclonal antisera. Blotting and detection were performed as described in the protocol for the enhanced chemiluminescence western blotting kit manufactured by Boehringer Mannheim (Arlington Heights, Ill.).

EXAMPLE 4
Electrophoretic Mobility Shift Assays

NF-κB activation was analyzed by electrophoretic mobility shift assay (EMSA) as described earlier (10). Briefly, $2 \times 10^6$ cells were washed with cold phosphate-buffered saline (PBS) and suspended in 0.4 ml of lysis buffer (10 mM HEPES pH 7.9, 10 mM KCl, 0.1 mM EDTA, 0.1 mM EGTA, 1 mM DTT, 0.5 mM PMSF, 2.0 mg/ml leupeptin, 2.0 mg/ml aprotinin, and 0.5 mg/ml benzamidine). The cells were allowed to swell on ice for 15 minutes, after which 12.5 ml of 10% NP-40 was added. The tube was then vortexed vigorously for 10 seconds, and the homogenate was centrifuged for 30 seconds. The nuclear pellet was resuspended in 25 μl ice-cold nuclear extraction buffer (20 mM HEPES pH 7.9, 0.4 M NaCl, 1 mM EDTA, 1 mM EGTA, 1 mM DTT, 1 mM PMSF, 2.0 mg/ml leupeptin, 2.0 mg/ml aprotinin, and 0.5 mg/ml benzamidine), and incubated on ice for 30 minutes with intermittent mixing. Samples were centrifuged for 5 minutes at 4° C., and the supernatant (nuclear extract) was either used immediately or stored at −70° C. The protein content was measured by the method of Bradford, M. M., *Anal. Biochem.* 72:248–254 (1976).

Electrophoretic mobility shift assays were performed by incubating 4 mg of nuclear extract with 16 fmoles of $^{32}P$ end-labeled, 45-mer double-stranded NF-κB oligonucleotide (Nabel, G. and Baltimore, D., *Nature* 326:711–13, 1987) for 15 minutes at 37° C. The incubation mixture included 2–3 mg of poly-(dI-dC) in a binding buffer (25 mM HEPES pH 7.9, 0.5 mM EDTA, 0.5 mM DTT, 1% NP-40, 5% glycerol, and 50 mM NaCl). The DNA-protein complex formed was separated from free oligonucleotide on a 4.5% native polyacrylamide gel using buffer containing 50 mM Tris, 200 mM glycine pH 8.5, and 1 mM EDTA, and the gel then was dried. Specificity of binding was also examined by competition with the unlabeled oligonucleotide.

Figure 3A:
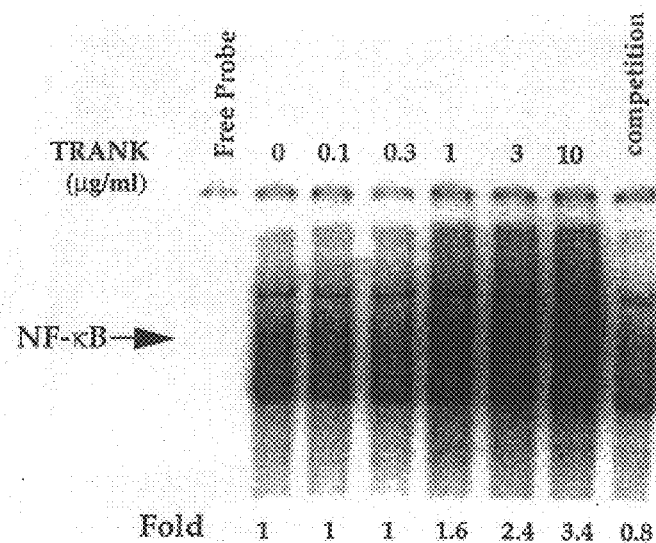
FIG. 3A demonstrates a dose response relation of TRANK-induced NF-κB activation. U-937 cells ($2 \times 10^6$/ml) were treated with different concentrations of TRANK for 30 min. at 37° C. and then assayed for NF-κB by electrophoretic mobility shift assay (EMSA).
Figure 3B:
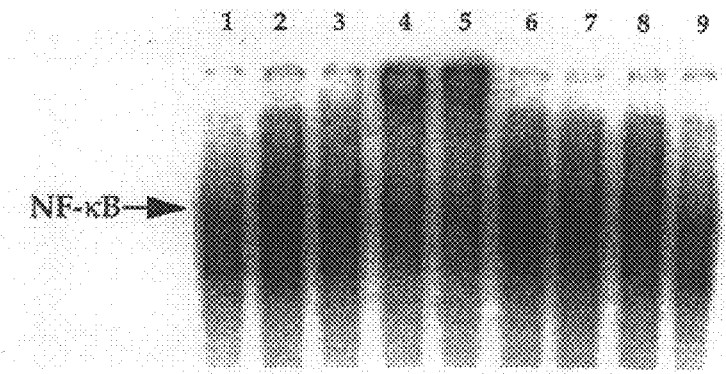
FIG. 3B shows supershift and specificity of NF-κB. Nuclear extracts from TRANK treated (lane 2) cells, were incubated for 15 min with anti-p50 (lane 3), anti-p65 (lane 4), antip50+anti-p65 (lane 5), anti-cyclin D1 (lane 6), anti-c-rel (lane 7), preimmune serum (lane 8) and cold NF-κB oligo probe (lane 9) and then assayed for NF-κB. Lane 1 is TRANK-untreated control.

Treatment of human myeloid U-937 cells with TRANK for 30 min revealed a dose-dependent activation of NF-κB by EMSA (FIG. 3A). The gel shift band was specific as it could be competed out with an unlabeled oligonucleotide and was supershifted by anti-p50 or anti-p65 antibody only (FIG. 3B) indicating that it is composed of p50 and p65 subunits (16).

Figure 3C:
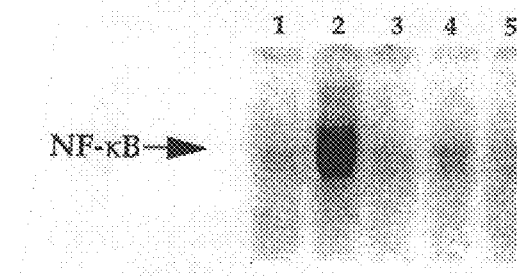
FIG. 3C depicts the effect of trypsinization and boiling on the ability of TRANK to activate NF-κB. TRANK was treated with 1% trypsin for 1 hour at room temperature and then checked for its ability to activate NF-κB in U-937 cells (lane 4). The effect of trypsin alone is shown in lane 3. TRANK was also boiled at 100° C. for 10 min and then checked for its activity (lane 5). Lanes 1 and 2 show the NF-κB status in untreated and TRANK-treated cells, respectively.
Figure 3D:
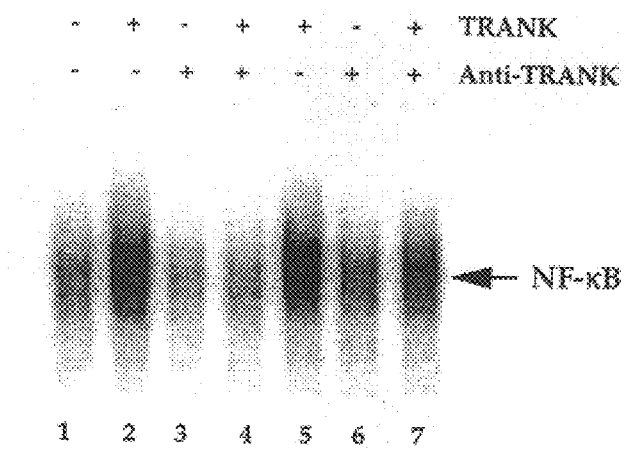
FIG. 3D demonstrates the effect of anti-TRANK polyclonal antibodies on TRANK-induced NF-κB in U-937 cells. TRANK was preincubated with anti-TRANK antibodies at a dilution of 1:100 (lanes 3 and 4) or 1:1000 (lanes 6 and 7) before exposure to cells.
Figure 3E:
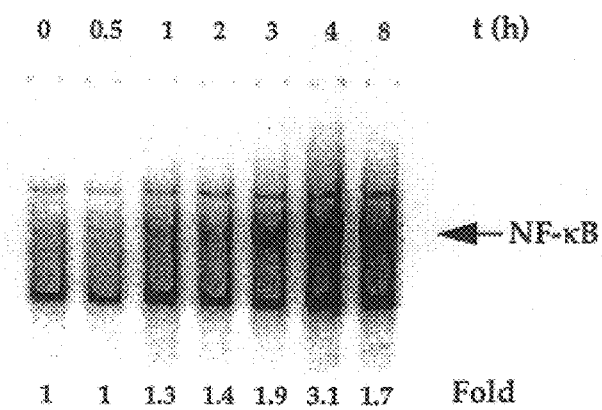
FIG. 3E shows U-937 cells treated with 1 μg/ml TRANK for different times at 37° C. and then were assayed for NF-κB activity.

To rule out that the activity observed was not the result of a contaminant, TRANK was treated with either 1% trypsin or heat-denaturation (FIG. 3C). Both treatments abolished TRANK-induced NF-κB activity, indicating that a protein is responsible for its activation. TRANK was also treated with polyclonal antibodies against the protein. This blocked NF-κB activation (FIG. 3D), indicating specificity of the effect. TRANK activated NF-κB in a time-dependent manner reaching a peak by 4 h and declining thereafter (FIG. 3E).

EXAMPLE 5
Western Blot Analysis of IκBα

Figure 3F:
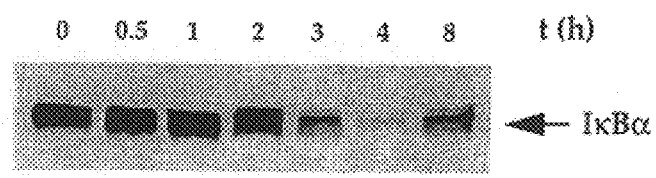
FIG. 3F depicts the time course of TRANK (1 μg/ml)-induced IκBα degradation in U-937 cells.

Cytoplasmic extracts of U-937 cells treated for different amounts of time with TRANK were used to examine IκBα degradation by western blot procedure as described (11). The degradation of IκBα in cells treated with TRANK for different times was also examined using western blot analysis. This showed that IκBα started to degrade at 3 hours, had almost completely degraded by 4 hours and started to be resynthesized at 8 hours (FIG. 3F).

EXAMPLE 6
NF-κB Luciferase Assay

In the NF-κB luciferase assay to assess the effect of TRANK on NF-κB-dependent luciferase gene transcription, a consensus NF-κB element was cloned into pSEAP-Basic vector (Clontech Labs Inc., Palo Alto, Calif.). A stable Jurkat cell line (Jurkat/NFκB-SEAP) that showed good activation in response to TNF was used in the assay. Test samples were added to Jurkat/NF-κKB-SEAP cells, and after 72 h the alkaline phosphatase activity was measured at 405 nm.

Figure 3G:
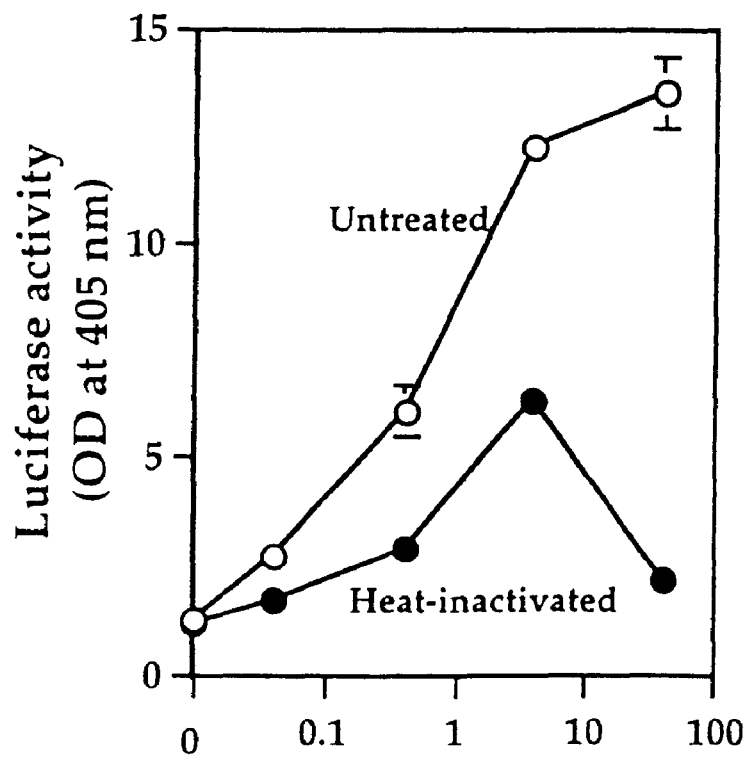
In FIG. 3G, TRANK is shown to activate NF-κB dependent gene transcription in Jurkat cells. Also shown is the effect of heat-denatured TRANK on this activity. NF-κB-driven luciferase activity was measured.

The results shown in FIG. 3G revealed that TRANK induced an approximately sevenfold increase in luciferase activity. Similar to NF-κB activation, heat-denaturation of TRANK significantly abolished its ability to induce luciferase activity (FIG. 3G).

EXAMPLE 7
Determination of Intracellular Adhesion Molecule (ICAM-1) Expression

The ICAM-1 expression was induced in EAhy 926 (hybrid cell line: human vascular endothelial cell line X human A549 lung carcinoma cell line) and in U-138MG (human umbilical vein endothelial cell line), as previously described (12). Levels of induced ICAM-1 were measured by ELISA using a monoclonal antibody (mAb) to human ICAM-1 (CD54) (Camfolio; Becton-Dickinson UK, Oxford, UK).

Figure 4A:
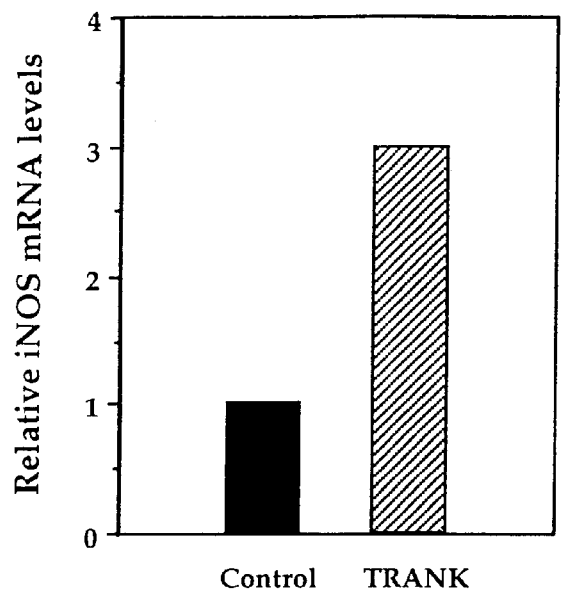
FIG. 4A shows the effect of TRANK on iNOS mRNA levels.
Figure 4B:
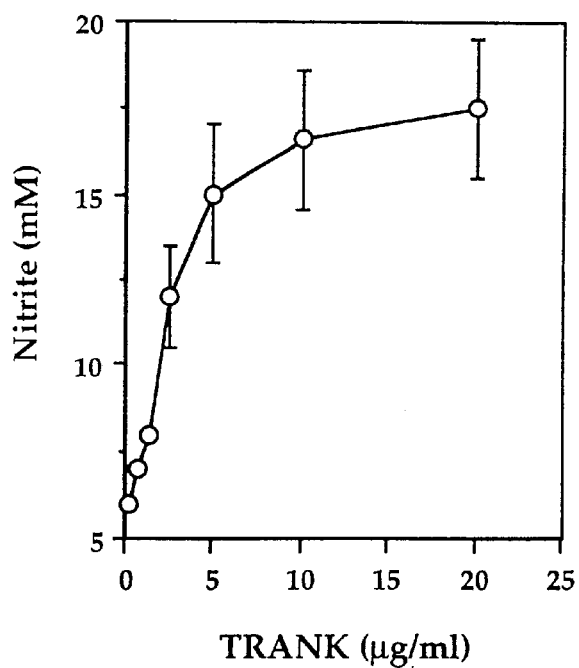
FIG. 4B depicts TRANK-induced release of nitric oxide from rat astrocytes.
Figure 4C:
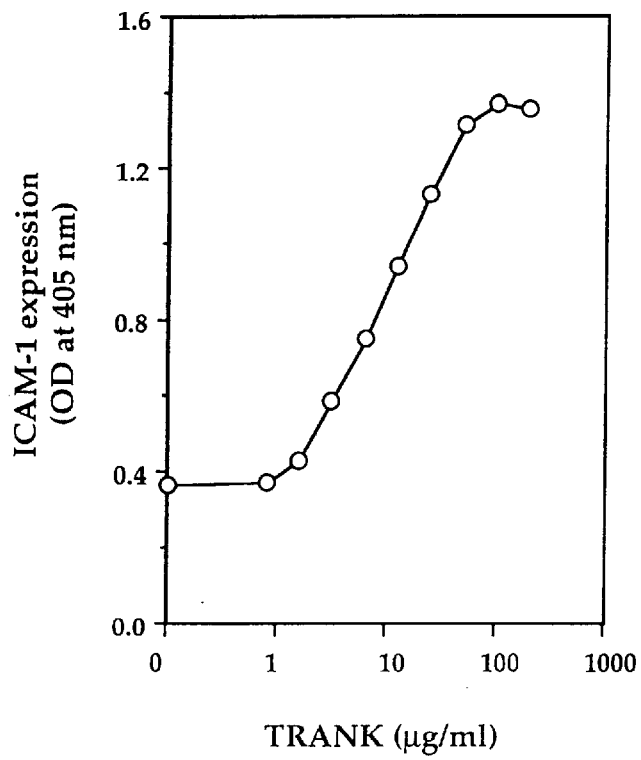
FIG. 4C demonstrates the effect of increasing doses of TRANK on expression of ICAM-1 in EAhy926 cells.

TRANK stimulated ICAM-1 expression in EAhy926 cells in a dose-dependent manner (FIG. 4C). Polyclonal antiserum to TRANK partially neutralized the TRANK-mediated enhancement of ICAM-1 expression (data not shown).

EXAMPLE 8
Measurement of Inducible Nitric Oxide Synthase (iNOS) and Nitrite

Rat cortical astrocytes cultures were treated with various concentrations of TRANK for 12 hours, RNA was isolated, and iNOS mRNA levels were measured by slot blot analysis as described (13). Levels of the stable nitric oxide metabolite, nitrite, were measured in the conditioned medium of TRANK treated cells (48 hours) after any nitrate had been converted into nitrite with nitrate reductase and NAPDH at 37° C. for 1 hour (13). Treatment of rat astrocyte cultures with TRANK resulted in stimulation of iNOS mRNA levels (FIG. 4A) and a dose-dependent increase in nitrite accumulation (FIG. 4B).

EXAMPLE 9
C-jun Kinase Assay

The c-Jun kinase (JNK) assay was performed according to the method described (14). Activation of JNK is another early event initiated by many other stress stimuli including cytokines via reactive oxygen species. Treatment of U-937 cells with TRANK led to an increase in JNK activity in a time-dependent fashion, until 120 min (8.5 fold increase) and a gradual decline in JNK activity thereafter (FIG. 4E).

EXAMPLE 10
Proliferation Assays

The effect of TRANK on the proliferation of human diploid foreskin fibroblasts was examined as described (15). Fibroblasts (5000/0.1 ml) were cultured with different concentrations of TRANK for 72 hours at 37° C. in 96-well plates and proliferation examined by tritiated thymidine uptake method.

Figure 4D:
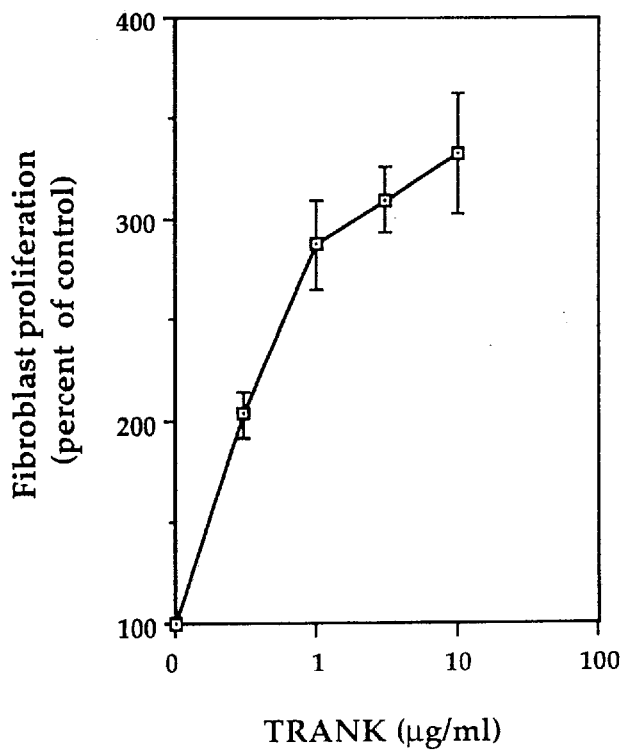
FIG. 4D shows the effect of TRANK on the proliferation of human diploid foreskin fibroblasts.
Figure 4E:
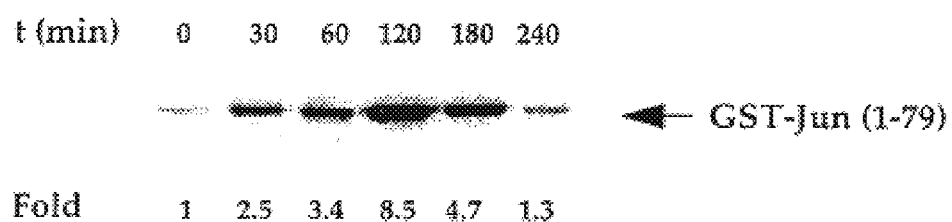
FIG. 4E illustrates TRANK-induced JNK activation. U-937 cells ($3 \times 10^6$/ml) were treated with 10 mg/ml TRANK for different times and then JNK was assayed.

Although TRANK was found to have no cytotoxic effect on most cells, it did induce the proliferation in a dose-dependent manner of normal human diploid fibroblasts (FIG. 4D). A greater than threefold increase in fibroblast proliferation over untreated control was observed. This indicated that TRANK is a growth factor for normal human fibroblast cells.

The following references were cited herein:
1. Sen, C. K., and L. Packer. 1996. Antioxidant and redox regulation of gene transcription. *FASEB J.* 10: 709.
2. Jin, D. Y., Z-C. Ho, S-G. Rhee, and K-T. Jeang. 1997. Regulatory role for a novel human thioredoxin peroxidase in NF-_B activation. *J. Biol. Chem.* 272: 30952.

3. Sauri, H., L. Butterfield, A. Kim, and H. Shau. 1995. Antioxidant function of recombinant human natural killer enhancing factor. *Biochem. Biophys. Res. Commun.* 208: 964.
4. Shau, H., R. K. Gupta, and S. H. Golub. 1993. Identification of a natural killer enhancing factor (NKEF) from human erythroid cells. *Cell. Immunol.* 147: 1.
5. Shau, H., L. H. Butterfield, R. Chiu, and A. Kim. 1994. Cloning and sequence analysis of candidate human natural killer-enhancing factor genes. *Immunogenetics* 40: 129.
6. Adams, M. D., A. R. Kerlavage, R. D. Fleischmann, R. A. Fuldner, C. J. Bult, N. H. Lee, E. F. Kirkness, K. G. Weinstock, J. D. Gocayne, and O. White. 1995. Initial assessment of human gene diversity and expression patterns based upon 83 million nucleotides of cDNA sequence. *Nature* 377 (Suppl.), 3.
7. Ni J, M. Abrahamson, M. Zhang, M. Fernandez, A. Grubb, J. Su, G-L. Yu, Y-L. Li, D. Parmelee, L. Xing, T. Coleman, S. Lima, R. Thotakura, N. Nguyen, M. Hesselberg, and R. Gentz. 1997. Cystatin E is a novel human cysteine proteinase inhibitor with structural resemblance to family 2 cystatins. *J Biol. Chem.* 272: 10853.
8. Altschul, S. F., and W. Gish. 1990. Basic local alignment search tool. *J. Mol. Biol.* 215: 403.
9. Johnson, C. V., R. H. Singer, and J. B. Lawrence. 1991 Fluorescent detection of nuclear RNA and DNA: implications for genome organization. *Methods Cell Biol.* 35: 73.
10. Chaturvedi, M., R. LaPushin, and B. B. Aggarwal. 1994. Tumor necrosis factor and lymphotoxin: qualitative and quantitative differences in the mediation of early and late cellular responses. *J Biol. Chem.* 269: 14575.
11. Reddy, S. A. G., M. M. Chaturvedi, B. G. Darnay, H. Chan, M. Higuchi, and B. B. Aggarwal. 1994. Reconstitution of NF_B activation induced by tumor necrosis factor requires membrane-associated components: comparison with pathway activated by ceramide. *J Biol. Chem.* 269: 25369.
12. Meager, A. 1996. Bioimmunoassays for proinflammatory cytokines involving cytokine-induced cellular adhesion molecule expression in human glioblastoma cell lines. *J. Immunol. Methods.* 190: 235.
13. Hu, J., F. Castets, J. L. Guevara, and L. J. Van Eldik. 1996. S100 beta stimulates inducible nitric oxide synthase activity and mRNA levels in rat cortical astrocytes. *J. Biol. Chem.* 271: 2543.
14. Haridas, V., B. G. Darnay, K. Natarajan, R. Heller, and B. B. Aggarwal. 1998. Overexpression of the p80 form of the TNF receptor induces apoptosis, NF-κB activation and c-Jun kinase activation: Comparison with the endogenous receptor. *J. Immunol.* 160, 3152.
15. Totpal, K., R. LaPushin, T. Kohno, B. G. Darnay, and B. B. Aggarwal. 1994. TNF and its receptor antibody agonist differ in mediation of cellular responses. *J. Immunol.* 153: 2248.
16. Anderson, M. T., F. J. T. Staal, and L. A. Herzenberg. 1994. Separation of oxidant-initiated and redox-regulated steps in the NF_kappa B signal transduction pathway. *Proc. Natl. Acad. Sci. U.S.A.* 91: 11527.
17. Xie, Q. W., Y. Kashiwabara, and C. Nathan. 1994.Role of transcription factor NF-kappa B/Rel in induction of nitric oxide synthase. *J. Biol. Chem.* 269:4705.
18. Aoudjit, F., N. Brochu, C. Stratowa, J. Hiscott, and M. Audette. 1997. Regulation of intercellular adhesion molecule-1 gene by tumor necrosis factor-alpha is mediated by the nuclear factor-kappaB heterodimers p65/p65 and p65/c-Rel in the absence of p50. *Cell Growth & Differen.* 8: 335.
19. Zhang, P., B. Liu, S-W. Kang, M-S. Seo, S-G. Rhee, and L-M. Obeid. 1997. Thioredoxin peroxidase is a novel inhibitor of apoptosis with a mechanism distinct from that of Bcl-2. *J. Biol. Chem.* 272: 30615.
20. Matsuda M., H. Masutani, H. Nakamura, S. Miyajima, A. Yamauchi, S. Yonehara, A. Uchida, K. Irimajiri, A. Horiuchi, and J. Yodoi. 1991. Protective activity of adult T cell leukemia-derived factor (ADF) against tumor necrosis factor dependent cytotoxicity on U937 cells. *J Immunol.* 147: 837.
21. Schulze-Osthoff, K., H. Schenk, and W. Droge. 1995. Effects of thioredoxin on activation of transcription factor NF-kappa B. *Meth. Enzymol.* 252: 253.
22. Haridas, V., J. Ni, A. Meager, J. Su, G. -L. Yu, Y. Zhai, H. Kyaw, K. T. Akama., J. Hu, L. J. Van Eldik and B. B. Aggarwal. 1998. TRANK, a novel cytokine that activates NF-_B and c-Jun N-terminal kinase. *Journal of Immunology,* 161, 1–6 (1998).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting TRANK-mediated NF-κB activation in an individual in need of such treatment, comprising the step of administering an effective dose of an anti-TRANK antibody to said individual, wherein said antibody reacts with human TRANK (thioredoxin peroxidase-related activator of NF-κB and c-Jun N-terminal kinase) protein of SEQ ID No. 1, and wherein binding of said antibody to said TRANK protein inhibits TRANK-mediated activation of NF-κB.

2. A method for treating a pathophysiological state in a human wherein said state has an undesirable level of TRANK-mediated NF-κB activation, comprising the step of administering to said human an effective dose of an anti-TRANK antibody, wherein said antibody reacts with human TRANK (thioredoxin peroxidase-related activator of NF-κB and c-Jun N-terminal kinase) protein of SEQ ID No. 1, and wherein binding of said antibody to said TRANK protein inhibits TRANK-mediated activation of NF-κB.

3. The method of claim 2, wherein said pathological state is toxic shock, septic shock, acute phase response, viral infection, radiation susceptibility, atherosclerosis, cancer, acute inflammatory conditions or graft vs. host reaction.

* * * * *

UNITED STATES PATENT AND TRADEMARK OFFICE
CERTIFICATE OF CORRECTION

PATENT NO.    : 6,605,278 B1
DATED         : August 12, 2003
INVENTOR(S)   : Bharat B. Aggarwal It is certified that error appears in the above-identified patent and that said Letters Patent is hereby corrected as shown below:

<u>Column 2,</u>
Line 10, please replace the comma after "processes" with a semicolon.
Line 11, please capitalize "nitric".

<u>Column 3,</u>
Line 67, "antip50" should read -- anti-p50 --.

<u>Column 9,</u>
Line 53, please replace the comma after "160" with a colon.

<u>Column 10,</u>
Line 35, please replace the comma after "161" with a colon.

Signed and Sealed this

Sixteenth Day of March, 2004

JON W. DUDAS
*Acting Director of the United States Patent and Trademark Office*

SEQUENCE LISTING

```
<160> NUMBER OF SEQ ID NOS: 5

<210> SEQ ID NO 1
<211> LENGTH: 271
<212> TYPE: PRT
<213> ORGANISM: unknown
<220> FEATURE:
<223> OTHER INFORMATION: Amino acid sequence of TRANK
```

<400> SEQUENCE: 1

```
Met Glu Ala Leu Pro Leu Leu Ala Ala Thr Thr Pro Asp His Gly
                 5                  10                  15

Arg His Arg Ser Cys Phe Cys Leu Pro Leu Leu Leu Phe Leu Leu
                20                  25                  30

Pro Ala Gly Ala Val Gln Gly Trp Glu Thr Glu Glu Arg Pro Arg
                35                  40                  45

Thr Arg Glu Glu Glu Cys His Phe Tyr Ala Gly Gly Gln Val Tyr
                50                  55                  60

Pro Gly Glu Ala Ser Arg Val Ser Val Ala Asp His Ser Leu His
                65                  70                  75

Leu Ser Lys Ala Lys Ile Ser Lys Pro Ala Pro Tyr Trp Glu Gly
                80                  85                  90

Thr Ala Val Ile Asp Gly Glu Phe Lys Glu Leu Lys Leu Thr Asp
                95                 100                 105

Tyr Arg Gly Lys Tyr Leu Val Phe Phe Phe Tyr Pro Leu Asp Phe
               110                 115                 120

Thr Phe Val Cys Pro Thr Glu Ile Ile Ala Phe Gly Asp Arg Leu
               125                 130                 135

Glu Glu Phe Arg Ser Ile Asn Thr Glu Val Val Ala Cys Ser Val
               140                 145                 150

Asp Ser Gln Phe Thr His Leu Ala Trp Ile Asn Thr Pro Arg Arg
               155                 160                 165

Gln Gly Gly Leu Gly Pro Ile Arg Ile Pro Leu Leu Ser Asp Leu
               170                 175                 180

Thr His Gln Ile Ser Lys Asp Tyr Gly Val Tyr Leu Glu Asp Ser
               185                 190                 195

Gly His Thr Leu Arg Gly Leu Phe Ile Ile Asp Asp Lys Gly Ile
               200                 205                 210

Leu Arg Gln Ile Thr Leu Asn Asp Leu Pro Val Gly Arg Ser Val
               215                 220                 225

Asp Glu Thr Leu Arg Leu Val Gln Ala Phe Gln Tyr Thr Asp Lys
               230                 235                 240

His Gly Glu Val Cys Pro Ala Gly Trp Lys Pro Gly Ser Glu Thr
               245                 250                 255

Ile Ile Pro Asp Pro Ala Gly Lys Leu Lys Tyr Phe Asp Lys Leu
               260                 265                 270

Asn
```

<210> SEQ ID NO 2
<211> LENGTH: 199
<212> TYPE: PRT
<213> ORGANISM: unknown
<220> FEATURE:
<223> OTHER INFORMATION: Amino acid sequence of region of natural killer cell-enhancing factor-A, NKEF-A, homologous to TRANK

<400> SEQUENCE: 2

```
Met Ser Ser Gly Asn Ala Lys Ile Gly His Pro Ala Pro Asn Phe
                 5                  10                  15

Lys Ala Thr Ala Val Met Pro Asn Gly Gln Phe Lys Asp Ile Ser
                20                  25                  30

Leu Ser Asp Tyr Lys Gly Lys Tyr Val Val Phe Phe Phe Tyr Pro
                35                  40                  45

Leu Asp Phe Thr Phe Val Cys Pro Thr Glu Ile Ile Ala Phe Ser
```

```
                  50                  55                  60
Asp Arg Ala Glu Glu Phe Lys Lys Leu Asn Cys Gln Val Ile Gly
                65                  70                  75
Ala Ser Val Asp Ser His Phe Cys His Leu Ala Trp Val Asn Thr
                80                  85                  90
Pro Lys Lys Gln Gly Gly Leu Gly Pro Met Asn Ile Pro Leu Val
                95                 100                 105
Ser Asp Pro Lys Arg Thr Ile Ala Gln Asp Tyr Gly Val Leu Lys
               110                 115                 120
Ala Asp Glu Gly Ile Ser Phe Arg Gly Leu Phe Ile Ile Asp Asp
               125                 130                 135
Lys Gly Ile Leu Arg Gln Ile Thr Val Asn Asp Pro Pro Cys Cys
               140                 145                 150
Arg Ser Val Asp Glu Thr Leu Arg Leu Val Gln Ala Phe Gln Phe
               155                 160                 165
Thr Asp Lys His Gly Glu Val Cys Pro Ala Gly Trp Lys Pro Gly
               170                 175                 180
Ser Asp Thr Ile Lys Pro Asp Val Pro Lys Thr Lys Glu Tyr Phe
               185                 190                 195

Ser Lys Gln Lys

<210> SEQ ID NO 3
<211> LENGTH: 198
<212> TYPE: PRT
<213> ORGANISM: unknown
<220> FEATURE:
<223> OTHER INFORMATION: Amino acid sequence of region of thioredoxin
      peroxidase, NKEF-B, homologous to TRANK

<400> SEQUENCE: 3

Met Ala Ser Gly Asn Ala Arg Ile Gly Lys Pro Ala Pro Asp Phe
                 5                  10                  15
Lys Ala Thr Ala Val Val Asn Gly Ala Phe Lys Glu Val Lys Leu
                20                  25                  30
Ser Asp Tyr Lys Gly Lys Tyr Val Val Leu Phe Phe Tyr Pro Leu
                35                  40                  45
Asp Phe Thr Phe Val Cys Pro Thr Glu Ile Ile Ala Phe Ser Asn
                50                  55                  60
Arg Ala Glu Asp Phe Arg Lys Leu Gly Cys Gln Val Ile Gly Val
                65                  70                  75
Ser Val Asp Ser Gln Phe Asn His Leu Ala Trp Val Asn Thr Pro
                80                  85                  90
Arg Lys Glu Gly Gly Leu Gly Pro Leu Asn Ile Pro Leu Leu Gly
                95                 100                 105
Asp Val Thr Arg Arg Leu Ser Glu Asp Tyr Gly Val Leu Lys Thr
               110                 115                 120
Asp Glu Gly Ile Ala Tyr Arg Gly Leu Phe Ile Ile Asp Gly Lys
               125                 130                 135
Gly Val Leu Arg Gln Ile Thr Val Asn Asp Pro Pro Cys Cys Arg
               140                 145                 150
Ser Val Asp Glu Ala Leu Arg Leu Val Gln Ala Phe Gln Tyr Thr
               155                 160                 165
Asp Glu His Gly Glu Val Cys Pro Ala Gly Trp Lys Pro Gly Ser
               170                 175                 180
Asp Thr Ile Lys Pro Asn Val Asp Asp Ser Lys Glu Tyr Phe Ser
```

```
                    185                 190                195

Lys His Asn

<210> SEQ ID NO 4
<211> LENGTH: 199
<212> TYPE: PRT
<213> ORGANISM: unknown
<220> FEATURE:
<223> OTHER INFORMATION: Amino acid sequence of region of proliferation
      associated gene product, PAG, homologous to TRANK

<400> SEQUENCE: 4

Met Ser Ser Gly Asn Ala Lys Ile Gly His Pro Ala Pro Asn Phe
                  5                  10                  15

Lys Ala Thr Ala Val Met Pro Asn Gly Gln Phe Lys Asp Ile Ser
                 20                  25                  30

Leu Ser Asp Tyr Lys Gly Lys Tyr Val Val Phe Phe Phe Tyr Pro
                 35                  40                  45

Leu Asp Phe Thr Phe Val Cys Pro Thr Glu Ile Ile Ala Phe Ser
                 50                  55                  60

Asp Arg Ala Glu Glu Phe Lys Lys Leu Asn Cys Gln Val Ile Gly
                 65                  70                  75

Ala Ser Val Asp Ser His Phe Cys His Leu Ala Trp Val Asn Thr
                 80                  85                  90

Pro Lys Lys Gln Gly Gly Leu Gly Pro Met Asn Ile Pro Leu Val
                 95                 100                 105

Ser Asp Pro Lys Arg Thr Ile Ala Gln Asp Tyr Gly Val Leu Lys
                110                 115                 120

Ala Asp Glu Gly Ile Ser Phe Arg Gly Leu Phe Ile Ile Asp Asp
                125                 130                 135

Lys Gly Ile Leu Arg Gln Ile Thr Val Asn Asp Leu Pro Val Gly
                140                 145                 150

Arg Ser Val Asp Glu Thr Leu Arg Leu Val Gln Ala Phe Gln Phe
                155                 160                 165

Thr Asp Lys His Gly Glu Val Cys Pro Ala Gly Trp Lys Pro Gly
                170                 175                 180

Ser Asp Thr Ile Lys Pro Asp Val Gln Lys Ser Lys Glu Tyr Phe
                185                 190                 195

Ser Lys Gln Lys

<210> SEQ ID NO 5
<211> LENGTH: 257
<212> TYPE: PRT
<213> ORGANISM: unknown
<220> FEATURE:
<223> OTHER INFORMATION: Amino acid sequence of region of murine
      erythroleukemia related, MER5, homologous to TRANK

<400> SEQUENCE: 5

Met Ala Ala Ala Ala Gly Arg Leu Leu Trp Ser Ser Val Ala Arg
                  5                  10                  15

His Ala Ser Ala Ile Ser Arg Ser Ile Ser Ala Ser Thr Val Leu
                 20                  25                  30

Arg Pro Val Ala Ser Arg Arg Thr Cys Leu Thr Asp Ile Leu Trp
                 35                  40                  45

Ser Ala Ser Ala Gln Gly Lys Ser Ala Phe Ser Thr Ser Ser Ser
                 50                  55                  60
```

```
Phe His Thr Pro Ala Val Thr Gln His Ala Pro Tyr Phe Lys Gly
            65                  70                  75

Thr Ala Val Val Asn Gly Glu Phe Lys Glu Leu Ser Leu Asp Asp
            80                  85                  90

Phe Lys Gly Lys Tyr Leu Val Leu Phe Phe Tyr Pro Leu Asp Phe
            95                  100                 105

Thr Phe Val Cys Pro Thr Glu Ile Val Ala Phe Ser Asp Lys Ala
            110                 115                 120

Asn Glu Phe His Asp Val Asn Cys Glu Val Val Ala Val Ser Val
            125                 130                 135

Asp Ser His Phe Ser His Leu Ala Trp Ile Asn Thr Pro Arg Lys
            140                 145                 150

Asn Gly Gly Leu Gly His Met Asn Ile Thr Leu Leu Ser Asp Ile
            155                 160                 165

Thr Lys Gln Ile Ser Arg Asp Tyr Gly Val Leu Leu Glu Ser Ala
            170                 175                 180

Gly Ile Ala Leu Arg Gly Leu Phe Ile Ile Asp Pro Asn Gly Val
            185                 190                 195

Val Lys His Leu Ser Val Asn Asp Leu Pro Val Gly Arg Ser Val
            200                 205                 210

Glu Glu Thr Leu Arg Leu Val Lys Ala Phe Gln Phe Val Glu Thr
            215                 220                 225

His Gly Glu Val Cys Pro Ala Asn Trp Thr Pro Glu Ser Pro Thr
            230                 235                 240

Ile Lys Pro Ser Pro Thr Ala Ser Lys Glu Tyr Phe Glu Lys Val
            245                 250                 255

His Gln
```